(12) United States Patent
Fago et al.

(10) Patent No.: US 8,118,780 B2
(45) Date of Patent: Feb. 21, 2012

(54) HYDRAULIC REMOTE FOR A MEDICAL FLUID INJECTOR

(75) Inventors: Frank M. Fago, Mason, OH (US); James E. Knipfer, Ft. Wright, KY (US); Charles S. Neer, Cincinnati, OH (US)

(73) Assignee: Liebel-Flarsheim Company LLC, Hazelwood, MO (US)

( * ) Notice: Subject to any disclaimer, the term of this patent is extended or adjusted under 35 U.S.C. 154(b) by 2010 days.

(21) Appl. No.: 10/924,302

(22) Filed: Aug. 23, 2004

(65) Prior Publication Data

US 2005/0027238 A1 Feb. 3, 2005

Related U.S. Application Data

(62) Division of application No. 10/146,696, filed on May 15, 2002, now Pat. No. 6,780,170.

(51) Int. Cl.
*A61M 1/00* (2006.01)

(52) U.S. Cl. ........ 604/151; 604/207; 604/208; 604/209; 604/210; 604/211; 604/212; 604/213; 604/214; 604/215; 604/216; 604/217; 604/152; 604/153; 604/154; 604/155; 604/65; 604/66; 604/67; 604/95.01; 604/131; 604/140; 604/141

(58) Field of Classification Search .......... 604/207–217, 604/151–155, 65–67, 95.01, 131, 140, 141
See application file for complete search history.

(56) References Cited

U.S. PATENT DOCUMENTS

| | | | |
|---|---|---|---|
| 3,623,474 A | | 11/1971 | Heilman et al. |
| 4,006,736 A | | 2/1977 | Kranys et al. |
| 4,085,749 A | * | 4/1978 | Chambron .................... 604/143 |
| 4,325,399 A | * | 4/1982 | Frick ................................ 137/85 |
| 4,551,133 A | * | 11/1985 | Zegers de Beyl et al. ....... 604/66 |
| 4,624,658 A | * | 11/1986 | Mardorf et al. ................ 604/121 |
| 4,749,109 A | | 6/1988 | Kamen |
| 4,854,324 A | * | 8/1989 | Hirschman et al. ........... 600/432 |
| 4,955,558 A | * | 9/1990 | Machell et al. .............. 244/3.22 |
| 4,976,696 A | * | 12/1990 | Sanderson et al. ............ 604/154 |
| 5,004,472 A | * | 4/1991 | Wallace ........................ 606/194 |

(Continued)

FOREIGN PATENT DOCUMENTS

GB 2222952 3/1990

(Continued)

OTHER PUBLICATIONS

David M. Reilly, Adapters. adapter systems and method for use in connection with powered injectors for agitation of multicomponent fluids, Jun. 26, 2003. 2003/0117888 Publication.

*Primary Examiner* — Nicholas Lucchesi
*Assistant Examiner* — Scott Medway
(74) *Attorney, Agent, or Firm* — Marsh Fischmann & Breyfogle LLP (57) ABSTRACT

A hand-held remote for a medical fluid injector includes a syringe and a conduit which may be coupled to a pressure transducer on a control circuit of the injector. Movement of a plunger within a syringe body on the syringe creates a pressure which is sensed by the pressure transducer and the control circuit responds to the sensed pressure by causing fluid to be ejected from, or drawn into, a syringe mounted to the injector. The pressure developed by the remote provides tactile feedback to an operator for improved control over injections.

21 Claims, 6 Drawing Sheets

U.S. PATENT DOCUMENTS

| | | | |
|---|---|---|---|
| 5,019,037 A | 5/1991 | Wang et al. | |
| 5,021,046 A | 6/1991 | Wallace | |
| 5,045,833 A | 9/1991 | Smith | |
| 5,140,862 A * | 8/1992 | Pappalardo | 73/866.4 |
| 5,244,463 A | 9/1993 | Cordner, Jr. et al. | |
| 5,269,762 A * | 12/1993 | Armbruster et al. | 604/155 |
| 5,342,298 A * | 8/1994 | Michaels et al. | 604/65 |
| 5,370,123 A * | 12/1994 | Shinzato | 600/486 |
| 5,383,855 A * | 1/1995 | Nicholson et al. | 604/100.03 |
| 5,383,858 A | 1/1995 | Reilly et al. | |
| 5,423,746 A * | 6/1995 | Burkett et al. | 604/65 |
| 5,423,759 A | 6/1995 | Campbell | |
| 5,431,629 A | 7/1995 | Lampropoulos et al. | |
| 5,449,345 A * | 9/1995 | Taylor et al. | 604/100.03 |
| 5,573,515 A | 11/1996 | Wilson et al. | |
| 5,630,527 A * | 5/1997 | Beebe et al. | 222/1 |
| 5,700,245 A * | 12/1997 | Sancoff et al. | 604/145 |
| 5,704,912 A * | 1/1998 | Lawrence et al. | 604/97.02 |
| 5,733,230 A | 3/1998 | Sawchuck et al. | |
| 5,800,397 A | 9/1998 | Wilson et al. | |
| 5,868,710 A | 2/1999 | Battiato et al. | |
| 5,882,343 A | 3/1999 | Wilson et al. | |
| 5,899,880 A * | 5/1999 | Bellhouse et al. | 604/70 |
| 5,916,165 A | 6/1999 | Duchon et al. | |
| 5,925,022 A | 7/1999 | Battiato et al. | |
| 6,010,478 A * | 1/2000 | Bellhouse et al. | 604/70 |
| 6,050,450 A * | 4/2000 | Gardos | 222/1 |
| 6,099,502 A | 8/2000 | Duchon et al. | |
| 6,171,276 B1 * | 1/2001 | Lippe et al. | 604/67 |
| 6,179,569 B1 * | 1/2001 | Kojima et al. | 417/63 |
| 6,206,868 B1 * | 3/2001 | Parodi | 604/500 |
| 6,221,045 B1 | 4/2001 | Duchon et al. | |
| 6,344,030 B1 | 2/2002 | Duchon et al. | |
| 6,780,170 B2 | 8/2004 | Fago et al. | |
| 7,044,933 B2 * | 5/2006 | VanDiver et al. | 604/151 |
| 7,296,566 B2 * | 11/2007 | Alchas | 128/200.14 |

FOREIGN PATENT DOCUMENTS

| | | |
|---|---|---|
| WO | 9842257 | 10/1998 |

* cited by examiner

HYDRAULIC REMOTE FOR A MEDICAL FLUID INJECTOR

This application is a divisional of application Ser. No. 10/146,696 filed May 15, 2002, now U.S. Pat. No. 6,780,170, the disclosure of which is fully incorporated herein by reference in its entirety.

FIELD OF THE INVENTION

This invention relates to injectors for injecting fluid into living organisms.

BACKGROUND OF THE INVENTION

In many medical environments, a medical fluid is injected into a patient during diagnosis or treatment. One example is the injection of contrast media into a patient to improve CT, Angiographic, Magnetic Resonance or Ultrasound imaging, using a powered, automatic injector.

Injectors suitable for these and similar applications typically must use a relatively large volume syringe and be capable of producing relatively large flow rates and injection pressures. For this reason, injectors for such applications are typically motorized, and include a large, high mass injector motor and drive train. For ease of use, the motor and drive train are typically housed in an injection head, which is supported by a floor, wall, or ceiling mounted arm.

The injection head is typically mounted on the arm in a pivotal manner, so that the head may be tilted upward (with the syringe tip above the remainder of the syringe) to facilitate filling the syringe with fluid, and downward (with the syringe tip below the remainder of the syringe) for injection. Tilting the head in this manner facilitates removal of air from the syringe during filling, and reduces the likelihood that air will be injected into the subject during the injection process. Nevertheless, the potential for accidentally injecting air into a patient remains a serious safety concern.

In addition to the injection head discussed above, many injectors include a separate console for controlling the injector. The console typically includes programmable circuitry which can be used for automatic, programmed control of the injector, so that the operation of the injector can be made predictable and potentially synchronized with operations of other equipment such as scanners or imaging equipment.

Thus, at least part of the injection process is typically automatically controlled; however, the filling procedure, and typically some part of the injection procedure, are normally performed by an operator, using hand-operated movement controls on the injector head. Typically, the hand-operated movement controls include buttons for reverse and forward movement of the injector drive ram, to respectively fill and empty the syringe. In some cases, a combination of buttons is used to initiate movement of the ram or to control ram movement speed. The injector head also typically includes a gauge or display for indicating injection parameters to the operator, such as the syringe volume remaining, for the operator's use when controlling the injector head.

In many cardiology procedures, cardiologists often prefer to use hand-held syringes to administer contrast media to a patent whereby the cardiologist can "feel" the injection and carefully control the rate of injection as needed. Because a high pressure is required to push contrast media through a catheter, small hand syringes must be used if an operator desires to manually administer the contrast media. However, these small syringes must be refilled several times during the contrast injection procedure, thereby increasing the risk of introducing air into the syringe or catheter.

U.S. Pat. No. 6,221,045 to Duchon et al. discloses a hand-held remote which may be used to control the injection of contrast media with a powered injector. If an operator chooses to use a powered injector having conventional controls, the operator must rely on visual indicators from the injector to determine how to manipulate the control for optimum injection. The visual indicators typical of current injector systems do not provide operators with the physical sensing of the injection that they prefer. Thus, one drawback of current injector systems, including the hand-held control system of Duchon et al., is that they do not permit operators to physically sense the injections and thereby control the rate and volume of the injection.

Due to sterility requirements in medical environments, hand-held controls are typically provided as disposable items. Thus, another drawback of conventional hand-held controls which utilize electronic or digital signals to control the injections is that they are not disposable without prohibitive expense.

A need exists for a hand-held remote which may be used with a powered medical injector to control the injection of contrast media while providing tactile feedback to the operator and which solves various problems in the art, such as those mentioned above.

SUMMARY OF THE INVENTION

The present invention provides a simple and convenient means for remotely controlling the injection or aspiration of fluids into or out of a patient using a medical fluid injector while providing tactile feedback to the user of the medical fluid injector. In an exemplary embodiment, a hydraulic remote for use with a medical fluid injector includes a syringe with a plunger slidably disposed within the syringe body, a pressure transducer which may be coupled to the control circuit of a medical fluid injector, and a conduit which connects the syringe to the pressure transducer. As used herein to describe the remote, the term "hydraulic" refers to the use of a fluid, which may be a liquid or a gas. Accordingly, the hydraulic remote could also be described as a pneumatic remote. Movement of the plunger into and out of the syringe body causes a change in pressure within the syringe body. The pressure transducer senses this change in pressure through the conduit and the control circuit of the medical fluid injector responds to the change in pressure by injecting or withdrawing fluid from the patient. The pressure in the syringe may also be sensed by the user of the hand-held remote such that the remote provides a tactile feedback to the user that is indicative of the rate and volume of injection or aspiration. The syringe and conduit may be inexpensive, off-the-shelf items, thereby minimizing disposal and replacement costs.

In another exemplary embodiment, a medical fluid injector includes a hydraulic remote, as described above, and further includes a plunger drive ram, a motor for moving the drive ram, a second syringe attached to the injector. The plunger drive ram moves a plunger into and out of the second syringe to inject or aspirate fluid from a patient. The medical injector further includes a control circuit which controls the movement of the plunger in the second syringe and responds to pressure sensed by the pressure transducer to move the plunger drive ram into or out of the second syringe. The medical injector responds to an increased pressure sensed by the pressure transducer by moving the plunger drive ram at a rate related to the change in sensed pressure from the hydraulic remote.

In another exemplary embodiment, a medical fluid injector includes a hand-operated control mounted to the injector. A control circuit of the injector responds to movement of the hand-operated control to move a plunger drive ram into or out of a second syringe attached to the medical injector at a rate corresponding to movement of the hand-operated control. The medical injector further includes a hydraulic remote and the control circuit is configured to respond to actuation of the hydraulic remote or the hand-operated control by moving the plunger drive ram into or out of the second syringe.

In yet another exemplary embodiment, the medical injector further includes a second pressure transducer coupled to the control circuit and to the hydraulic remote. The control circuit responds to pressure sensed by the first pressure transducer to control the motion of the plunger drive ram into or out of the second syringe. The control circuit responds to the pressure sensed by the second pressure transducer to enable operation of the medical fluid injector when the pressure transducer senses a pressure above a preset threshold. Advantageously, the threshold pressure is set at a level such that injection or aspiration of fluid will cease when a user releases the plunger on the hydraulic remote.

In another exemplary embodiment of the present invention, a circuit board is couplable to an existing medical fluid injector to modify the injector so that it can be used with the hydraulic remote as described above.

In yet another exemplary embodiment, a method of controlling the injection or aspiration of fluid using a medical fluid injector having a hydraulic remote coupled to the injector includes the steps of moving a plunger of the hydraulic remote to generate a pressure, sensing the pressure generated by the hydraulic remote, and moving a plunger drive ram on the injector in response to the sensed pressure.

The features and objectives of the present invention will become more readily apparent from the following Detailed Description taken in conjunction with the accompanying drawings.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

DETAILED DESCRIPTION

The present invention provides a hand-held remote control which may be used with a medical injector to control the injection of fluids into a patient while providing tactile feedback to an operator of the injector. Furthermore, because the disposable components of the remote control are often available as off-the-shelf items, the cost of the disposable items are significantly reduced compared to currently available systems.

Figure 1:
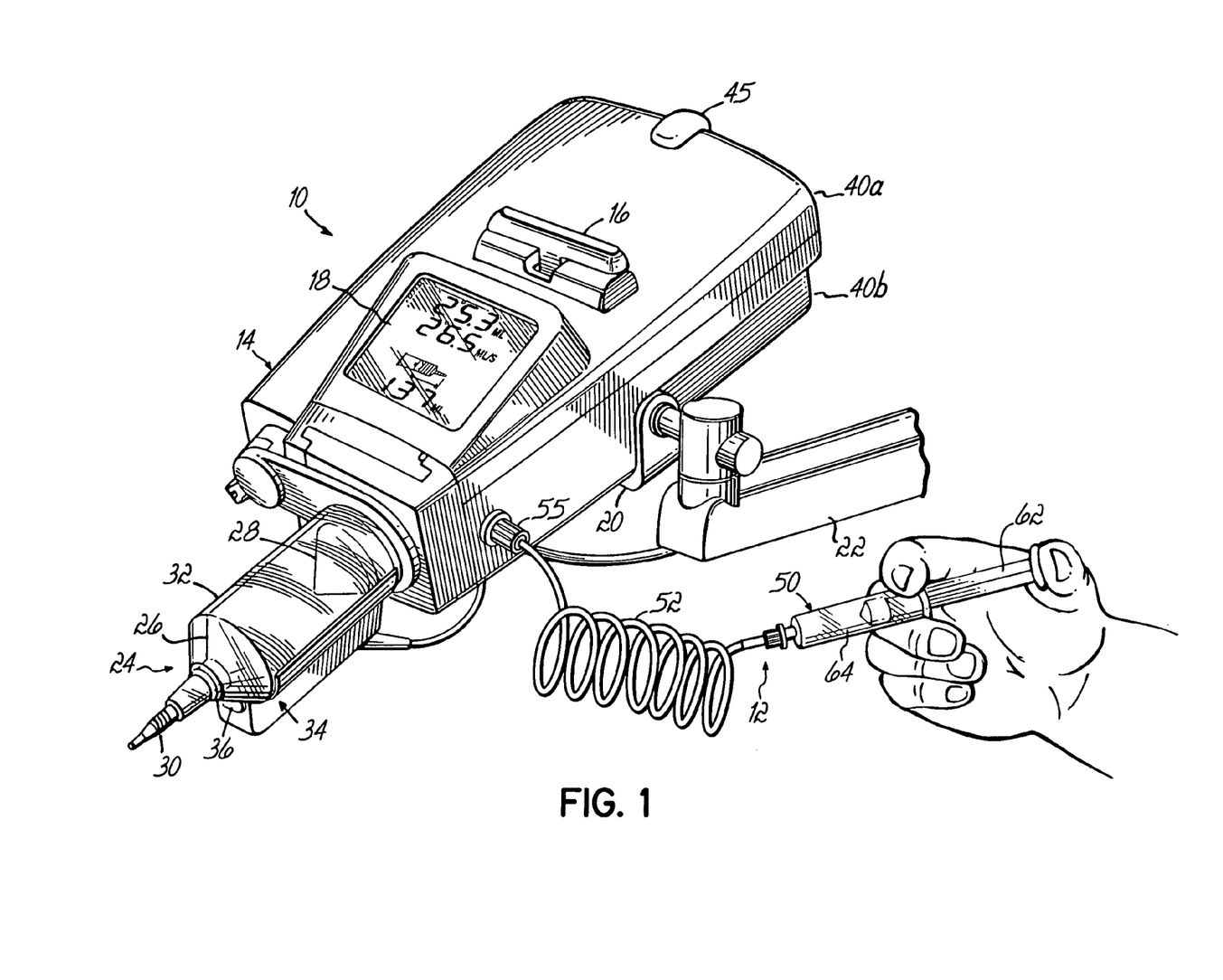
FIG. 1 is a perspective view of an exemplary medical fluid injector with an exemplary hydraulic remote of the present invention.

Referring to FIG. 1, there is shown an exemplary medical injector 10 including an exemplary hand-held remote 12 of the present invention. One such medical fluid injector is the Illumena model injector, available from Liebel-Flarsheim Company, Cincinnati, Ohio. The injector 10 includes a power head 14 housing an internal drive motor, a hand-operated movement control lever 16, and a display 18 for indicating to an operator the current status and operating parameters of the injector 10. The power head 14 may generally be supported on a carriage (not shown) by a mount 20 and an articulated support arm 22, as described more fully in U.S. Pat. No. 5,925,022 to Battiato et al., which is commonly held by the assignee of the present invention and herein incorporated by reference in its entirety. A syringe 24 including a syringe barrel 26 and a plunger 28 may be mounted on the power head 14 to interface with the internal drive motor (not shown) of the injector 10. The plunger 28 is coupled to a plunger drive ram (not shown) of the motor whereby the motor may cause the syringe plunger 28 to move along the syringe barrel 26 to inject contents of the syringe 24 or to draw fluids into the barrel 26 via discharge tip 30. The syringe 24 may be surrounded by a pressure jacket 32 which supports the outer walls of the syringe barrel 26. A heater blanket 34 may be mounted on a post 36 which extends from the power head 14, and abuts the exterior wall of pressure jacket 32 to heat the contents of the syringe 24 and maintain the temperature at approximately body temperature.

Figure 2:
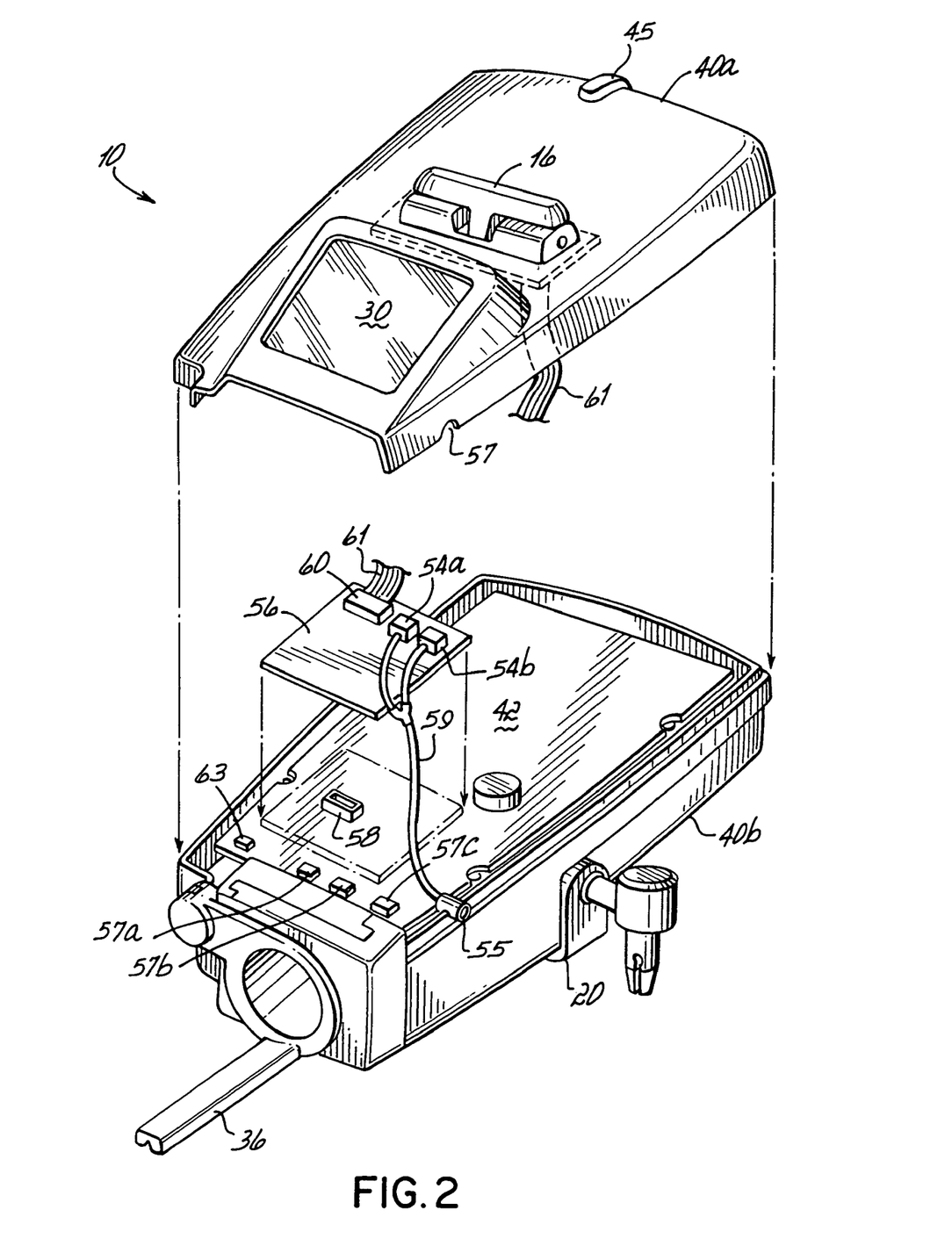
FIG. 2 is an exploded perspective view of the injector of FIG. 1.

Referring further to FIG. 2, the power head 14 further comprises a housing made up of a first housing portion 40a and a second housing portion 40b which enclose the internal drive motor and a control circuit 42 for controlling the motor. Manipulation of the hand-operated movement control lever 16 is sensed by the control circuit 42 to cause the plunger drive ram to inject or aspirate fluids from the syringe 24, as more completely described in U.S. Pat. No. 5,925,022 to Battiato et al. Alternatively, the injector 10 may be operated using the hydraulic remote 12.

Referring now to FIGS. 1 and 2, remote 12 includes a second syringe 50, conveniently sized to be hand-held, and a conduit 52 connecting an outlet of the syringe 50 to the injector 10. In an exemplary embodiment, the conduit 52 is a flexible tubing. Conduit 52 is coupled to at least one pressure transducer 54 which, in turn, is coupled to the control circuit 42 of the injector 10. In an exemplary embodiment, the conduit 52 is coupled to the pressure transducer 54 by a connector 55 which extends through an aperture 57 in the housing 40. A second conduit 59 extends from the connector to one or more pressure transducers 54. The pressure transducer 54 may either be provided directly on the control circuit 42, or alternatively, may be provided on a circuit board 56 that may be connected to the control circuit 42 of the injector 10. For example, the circuit board 56 containing the pressure transducer 54 may be configured to be connected to the control circuit 42 of the injector 10 at an interface 58 for receiving input from the control lever 16. The circuit board 56 may further include a connector 60 for receiving the input from the control lever 16 and adapted to be coupled to control lever 16, such as by electrical leads 61. Such a configuration advantageously permits the medical injector 10 to be operated by either the control lever 16 or the hydraulic remote 12.

Figure 3:
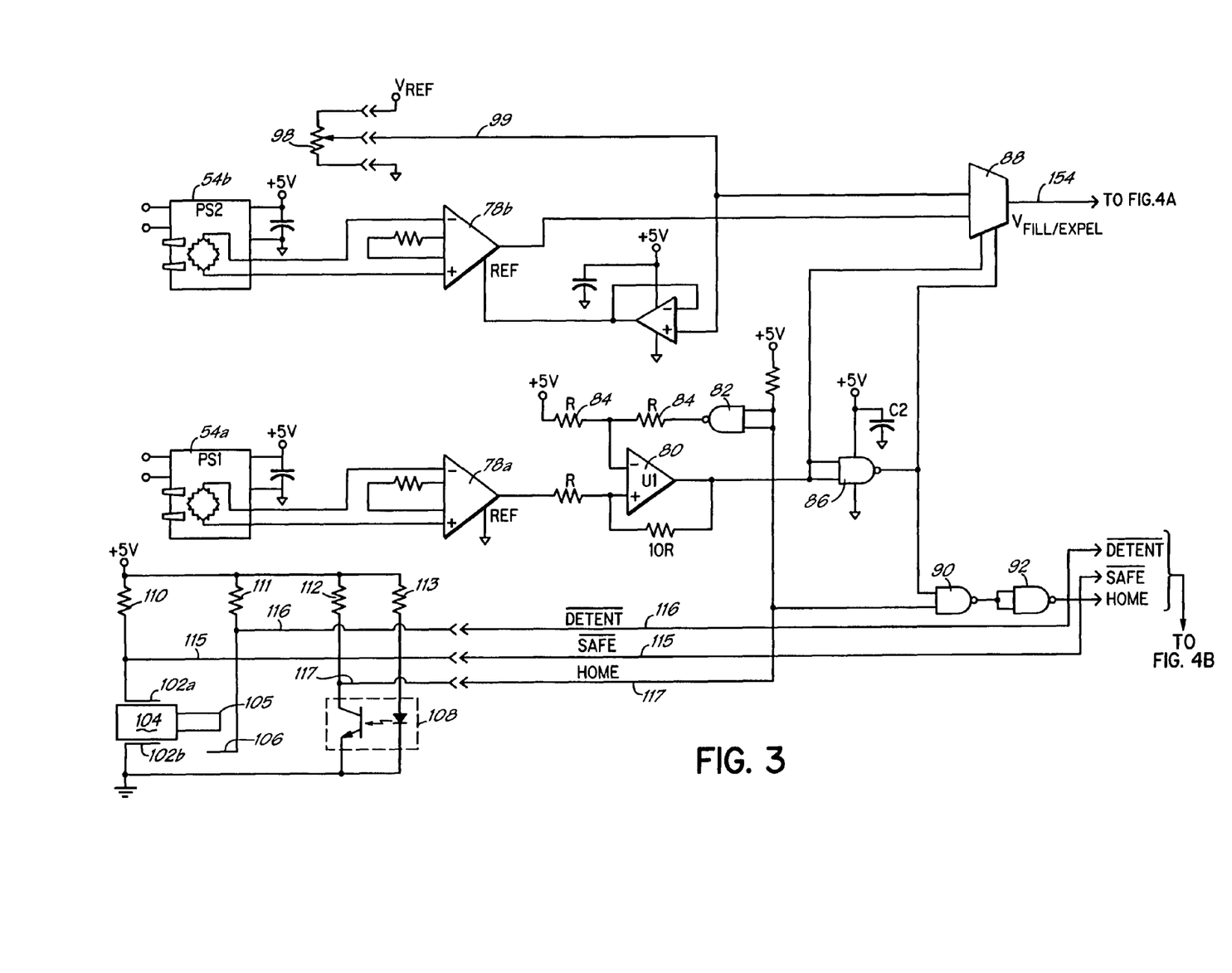
FIG. 3 is an electrical block diagram illustrating the circuitry of the hydraulic remote and hand control of the injector of FIG. 1.

Referring now to FIG. 3, circuit details of a power injector in accordance with the invention can be described. Pressure sensors 54a and 54b are active electromechanical transducers, which electrically form a balanced bridge. The potential across the bridge is reflective of the pressure being detected by the sensor 54a and 54b. Sensors 54a and 54b are each connected to differential amplifiers to apply gain to the differential voltage produced by the sensor. Differential amplifier 78a is connected to sensor 54a and produces a voltage, referenced to ground, in proportion to the magnitude of the pressure detected by sensor 54a. (The output of amplifier 78a is referenced to ground by a grounded connection at the REF input of amplifier 78a.) Differential amplifier 78b is connected to sensor 54b, and also produces a voltage in proportion to the magnitude of the pressure detected by sensor 54b. However, the voltage produced by amplifier 78b is referenced to the analog voltage obtained from potentiometer 98, for reasons to be explained below.

The output of differential amplifier 78a is coupled through a resistance R to the inverting input of a comparator 80. The output of comparator 80 is fed back to the noninverting input through a resistance 10R, thus introducing a hysteresis in the response of comparator 80. The noninverting input of comparator 80 has a voltage of approximately 2.5 volts when the output of NAND gate 82 is a logic "low", thus, in this condition, comparator 80 will produce a logic "high" signal whenever the input from differential amplifier 78a slews above approximately 2.5 volts. The gain of differential amplifier 78a is set so that an output of 2.5 volts is achieved whenever the pressure detected by pressure sensor 54a is above a minimum threshold, indicative of the use of the hand syringe 50 to manually control an injection. This threshold prevents unintended manual operation of the injector from the limited hydraulic pressure present in the hand syringe 50 as initially installed on the injector.

When the pressure sensed by sensor 54a exceeds the desired minimum threshold, and the output of NAND gate 82 is logic "low", then comparator 80 will produce a logic "high" output, which enables operation of the hand syringe 50 for manual injection control. The output of comparator 80 is coupled to a NAND gate wired as an inverter 86, and the output of comparator 80 and NAND inverter 86 are connected to the control inputs of an analog multiplexer 88. As a consequence of these connections, when comparator 80 produces a logic "high" output, multiplexer 88 delivers an analog signal from the output of differential amplifier 78b to line 154. When comparator 80 produces a logic "low" output, multiplexer 88 delivers an analog signal from the wiper of potentiometer 99 to line 154.

As elaborated in substantially greater detail in the above referenced U.S. patent of Battiato et al., rotation of the manual hand control 16 on the powerhead 14 also controls forward and reverse movement of the plunger. Rotation of the manual hand control is detected by a rotary potentiometer 98. The manual hand control is returned to a neutral position by return springs 102a and 102b. FIG. 3 illustrates potentiometer 98, which is connected between a reference voltage and ground to provide a voltage on line 99 indicative of the rotation of manual hand control 16. Return springs 102a and 102b of the manual hand control, and a flag/contact connected to and rotating with the hand control, also form circuit elements in FIG. 3. Return springs 102a and 102b are connected with a resistor 110 in a series connection between a digital +5 volt power supply and ground. A signal line 115 extending from between resistor 110 and spring 102a carries a logic voltage signal indicating whether a current-carrying electrical contact is completed between springs 102a and 102b and flag/contact 104. Under normal conditions, there should be an electrical path through this path to ground, holding the voltage on line 115 at a low level, indicating proper operation. However, if one of springs 102a or 102b fails, and no longer engages flag/contact 104, this electrical contact will be broken, and the voltage on line 115 will be elevated to a high level, indicating failure of a return spring. Although both return springs must fail before lever 16 may unintentionally deflect away from the home position, failure of just one spring can be detected by monitoring the voltage on line 115. Upon initial detection of such a failure, a warning may be given to the operator, or alternatively, the hand-operated movement control may disabled.

The hand control 16 further includes a detent spring 106, which similarly forms an electrical contact in a series connection with a resistor 111; a detent signal line 116 extends from between resistor 111 and the detent spring. If control lever 16 is not rotated into the detent spring, line 116 will be pulled to a high level, indicating that the control lever 16 is not at the detent. However, if control lever 16 is rotated such that flag 105 contacts detent spring 106, line 116 will be pulled to a low level, indicating that control lever 16 has been rotated to the detent. The signal on line 116 may be used in several ways. For example, the signal may be used to calibrate the hand-operated control so that the angle of lever rotation corresponding to the detent is equal to the ideal fill speed. Alternatively, the signal may be used to prevent reverse movement of the ram at a speed faster than the ideal fill speed. Finally, the signal may be used to establish a "dead zone" of motion, in which the ram will move at the ideal fill speed, while permitting the lever to be rotated beyond the "dead zone" to produce faster reverse speeds.

FIG. 3 also illustrates the circuit details of a flag detector 108; a light emitting diode is energized with a bias current via resistor 113; when light passes through the gap in detector 108 and strikes the base of a phototransistor in detector 108, the phototransistor draws current through resistor 112 to drive a home signal on line 117 to a low value, indicating that control lever 16 is not in its home position. Otherwise, if light is unable to pass to the base of the phototransistor in detector 108, current is not drawn through resistor 112 and the home signal on line 117 is pulled to a high value, indicating that control lever 16 is in its home position. The circuitry on FIG. 3 can thus use the home signal on line 117 to determine whether the hand control is in its home position.

Specifically, it can be seen that the home signal is connected through a NAND gate connected as an inverter 82, to a voltage divider comprised of equal valued resistors 84. The midpoint of resistors 84 is connected to the inverting input of comparator 80. The noninverting input of comparator 80 is connected to the output of differential amplifier 78a, as discussed above. As a consequence of these connections, when the home signal on line 117 is low (indicating that the hand control 16 is in use), the output of NAND gate 82 and the midpoint of resistors 84 will have a logic "high" value. As a result, the output of comparator 80 will have a logic "low" value regardless of the signal present at the output of differential amplifier 78a. As noted, under these conditions, the analog voltage on line 99 from the wiper of potentiometer 98 is delivered through analog multiplexer 88 to line 154. Alternatively, when the hand control is in its home position, if the pressure in hand syringe 50 is above the established minimum threshold, then the output of comparator 80 will have a logic "high" value and the analog voltage from differential amplifier 78b is delivered through analog multiplexer 88 to line 154.

As can be seen with the above background, the analog voltage on line 154 reflects the desired manual movement, whether indicated by rotation of the hand control 16 or by pressure on the hand syringe 50. As noted above, the voltage produced by differential amplifier 78b is referenced to the analog voltage on line 99 from the wiper of potentiometer 98. Since the hand syringe 50 is only enabled and may only be used while the hand control 16 is in its home position, this connection causes the voltage output by differential amplifier 78b to be referenced to the same voltage produced by the potentiometer 98 on its wiper terminal 99 when in the home position. Thus, the analog voltage produced by differential amplifier 78b deviates from the same baseline voltage as the analog voltage produced by hand control 16 potentiometer 98.

It will be noted that the detent and safe signals on lines 115 and 116 are delivered to the microprocessor shown in FIG. 4B, discussed further below. A third "home" signal is also delivered to the microprocessor. This signal is produced by a first NAND gate 90, via a second NAND gate 92 connected as an inverter, so that the "home" signal delivered to the microprocessor will have a "high" value whenever the hand control 16 is in its "home" position and the pressure sensed by sensor 54a is below the established threshold (causing comparator 80 to produce a "low" output signal). Thus, the "home" signal output by NAND gate 92 identifies those conditions where no manual movement is being requested either through hand control 16 or hand syringe 50.

Figure 4A:
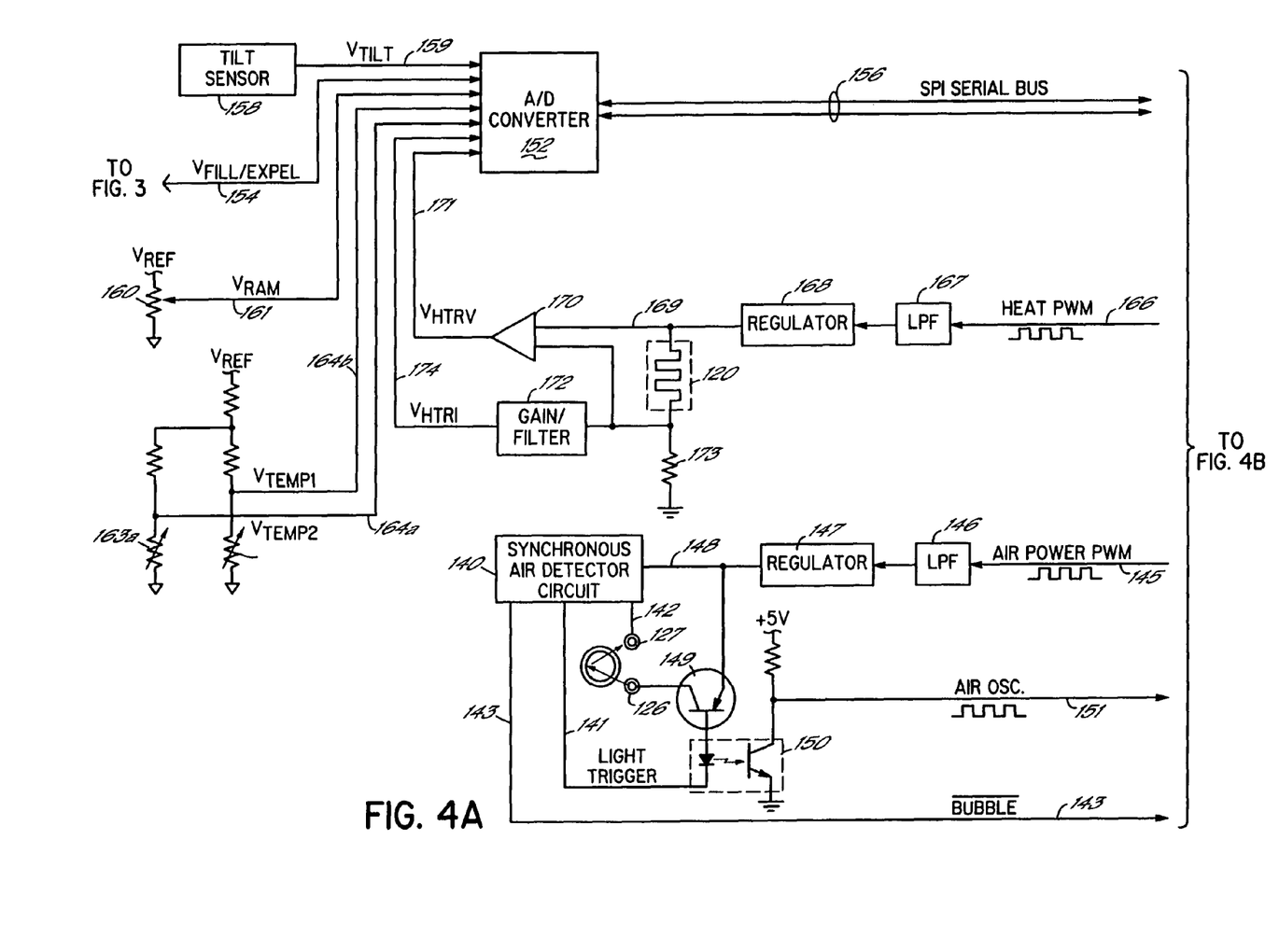
FIG. 4A is an electrical block diagram of interface circuitry connected to the circuitry of FIG. 3 and other external sensors of the injector of FIG. 1.

Now turning to FIG. 4A, the electrical circuit details of the air detection module, and other analog electrical systems, can be elaborated. Specifically, the air detection module incorporates therein, a commercially available synchronous detection circuit 140, which includes an internal oscillator generating trigger pulses on line 141, and, contemporaneously with each trigger pulse, detects electrical signals on line 142 indicating that light has been received at light sensor 127. So long as light is detected contemporaneously with each trigger pulse, a high level signal is produced on line 143. Due to the application to which circuit 140 is applied in accordance with the invention, the signal on line 143 indicates whether air has been detected in the neck of the syringe 24.

The control circuit of power head 14 may control the light intensity applied to the air bubble detector, to control the sensitivity of the detector. To do so, the control circuit produces a pulse width modulated (PWM) digital signal on line 145. This PWM signal is filtered by a low-pass filter circuit 146 to produce an analog control voltage, which controls an adjustable regulator 147 to produce the power signal on line 148 for circuit 140.

In response to the trigger signal on line 141, a PNP opto-transistor 149 is turned "on", causing the power signal on line 148 to energize light source 126. Thus, the voltage of the power signal on line 148 directly affects the intensity of light generated by light source 126.

So that the control circuit may monitor the air detector circuit 140 for possible failures, the trigger signal on line 141 is connected to the base of PNP opto-transistor 149 via a light emitting diode in an opto-isolator 150. Accordingly, the opto-transistor in opto-isolator 150 will turn "on" whenever the trigger signal is activated, causing a "low" level to appear on line 151. Thus, if the synchronous air detector circuit 140 is operating properly and producing periodic trigger signals, pulses will appear on line 151, which can be detected by the control circuit to verify that the oscillator in circuit 140 is operating properly.

FIG. 4A also illustrates the analog-to-digital (A/D) converter 152 incorporated into the power head control circuit for quantizing analog signals produced by various electrical elements. One such signal is the voltage produced by the circuitry of FIG. 3 on line 154, which is representative of the rotational position of the fill/expel hand control 16, or the pressure in the hand syringe 50. A/D converter 152 converts the analog voltage on line 154 to a digital signal on a "SPI" serial interface bus 156, upon request from the CPU (see FIG. 4B), so that the CPU can determine the position of hand control 16 or pressure in the hand syringe 50 and react accordingly.

Other analog voltages are also input to A/D converter 152. Specifically, a single-chip accelerometer is configured as a tilt sensor 158, to produce an analog voltage on line 159 indicative of the angle of tilt of sensor 158. (A suitable single chip accelerometer for this purpose is available from Analog Devices of Norwood, Mass. as part no. ADXL05AH.) Sensor 158 is mounted to circuit board 55, and therefore produces an output voltage indicative of the tilt of power head 14 relative to the direction of Earth gravity. This analog tilt signal is converted and input to the CPU for use, as noted below; in controlling the display and other operational features of power head 14.

A third analog signal is produced by a linear potentiometer 160, the wiper of which is mechanically connected to the plunger drive ram, and moved in response to movement of the plunger drive ram. Thus, the voltage of the wiper on line 161 is an analog signal representative of the position of the ram between its rearward most and forward most positions. This signal is converted and used by the CPU to determine the position of the ram and, among other things, the syringe volume remaining.

Two additional analog signals are produced by thermistors 163A and 163b, which are series connected with bias resistors to produce voltages on lines 164a and 164b which reflect the temperature of the thermistors. The temperature measurement obtained from these thermistors is then used to control the power applied through the heater blanket 34 to warm the fluid in the syringe 24. Specifically, the heat power applied to the syringe is varied proportion to the ambient temperature, as measured by thermistors 163a and 164a, to maintain the fluid at the target temperature, e.g., 30 degrees Celsius.

Thermistors 163a and 163b are duplicative, that is, both measure the same temperature and their measurements are compared to ensure near agreement. As a result, failure of a thermistor can be detected from disagreement between the temperature readings obtained from the thermistors, preventing loss of temperature control.

Thermistors 163a and 163b may be mounted internally to power head 14, on circuit board 42. Alternatively, thermistors 163a and 163b may be external to the housing, to ensure more accurate temperature readings, or both options may be allowed by providing internally-mounted thermistors which can be disabled if substitute externally-mounted thermistors are connected to the power head 14.

As noted above, using thermistors 163a and 163b, power head 14 controls the heat power applied to the syringe 24 through heater blanket 34. To perform this function, the CPU (see FIG. 4B) produces a pulse width modulated (PWM) control signal on line 166 which is used to control the heat power applied to the heater blanket filament 120. Specifically, the PWM signal on line 166 is low pass filtered by filter 167, producing an analog control signal which controls an adjustable regulator 168. The output of regulator 168 on line 169 is a variable voltage which is applied across heater blanket filament 120, causing heater filament 120 to produce heat.

An instrumentation amplifier 170 filters and conditions the voltage across filament 120 to produce an analog output signal on line 171 which is proportional to the voltage applied to the heater blanket filament 120.

A sense resistor 173 is series connected with heater filament 120, so that the current in heater filament 120 passes through sense resistor 173, producing a voltage on sense resistor proportional to the current flowing through heater filament 120. Sense resistor has a resistance substantially smaller than that of heater filament 120, so that the small voltage drop across sense resistor 173 is not a substantial percentage of the voltage drop across heater filament 120.

The voltage drop across sense resistor 173 is amplified and filtered by a gain/filter circuit 172, producing an analog voltage on line 174 which is proportional to the current flowing through heater filament 120.

Lines 171 and 174 are connected to A/D converter 152, and the voltages on lines 171 and 174 are converted thereby to digital signals which can be read by the CPU. Accordingly, the CPU can determine the current and voltage drop across heater filament 120, and use these values to determine the heat output of heater filament 120. This permits the CPU to perform closed-loop control of the heater blanket heat output, as discussed more thoroughly in U.S. Pat. No. 5,925,022.

Figure 4B:
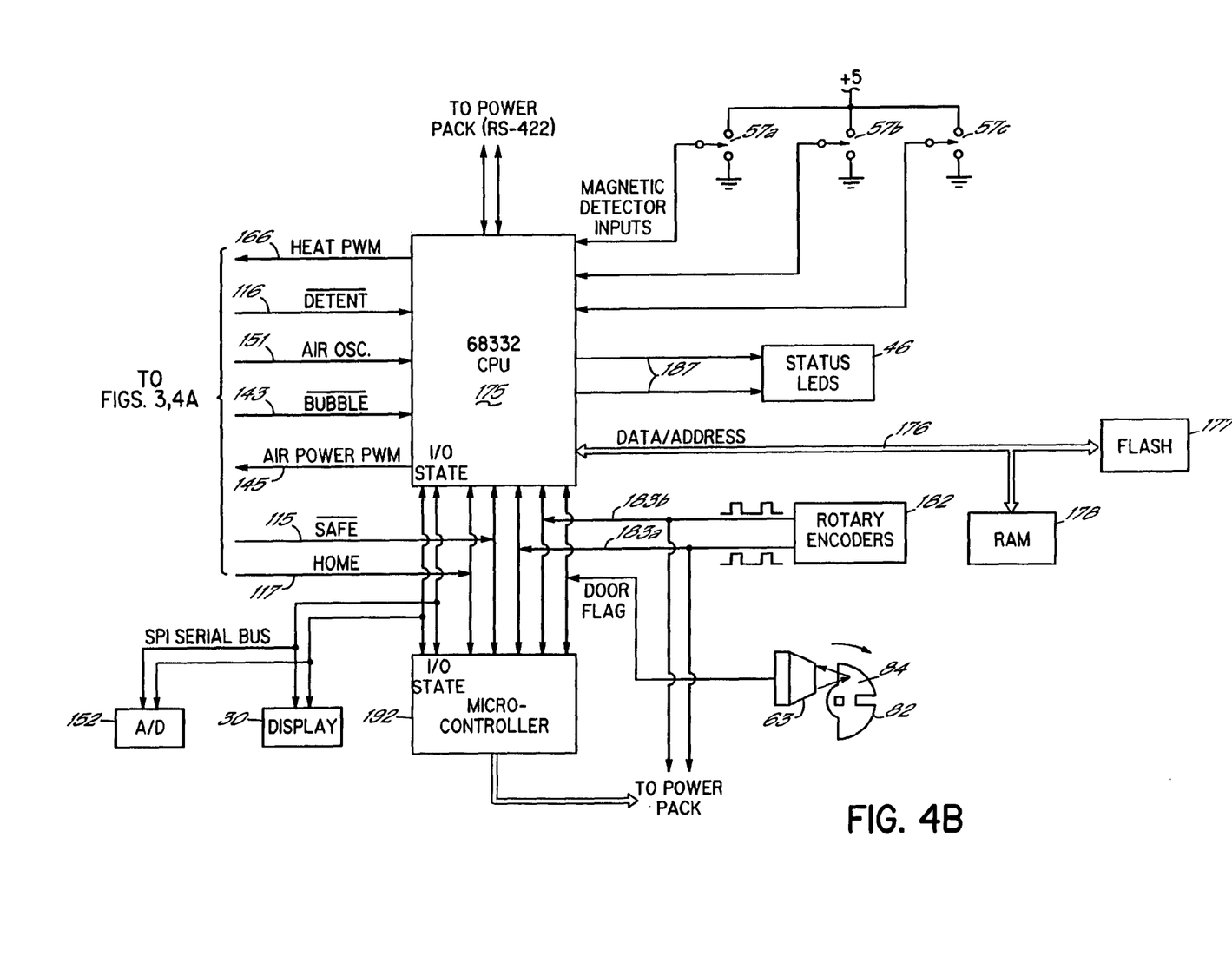
FIG. 4B is an electrical block diagram of the processor and peripheral circuitry of the injector of FIG. 1.

Referring now to FIG. 4B, the connections to the CPU of the power head 14 can be understood. The CPU 175, which may be a 68332 microprocessor, available from Motorola, controls data and address busses 176 connecting CPU 175 to random access memory (RAM) 178 and a flash memory 177. CPU 175 also controls an SPI serial interface bus 156 for communicating with A/D converter 152, display 30 and a monitor microcontroller 192. CPU 175 further includes an RS-422 serial interface 179 connecting CPU 175 to a CPU in the power pack (see FIG. 4C).

CPU 175 includes a number of digital data input lines for monitoring operation of power head 14. Specifically, CPU 175 receives the detent signal on line 116, safe signal on line 115 and home signal on line 117, enabling CPU to receive input on the state of operation of the hand-operated controls (lever and syringe) as discussed above. CPU 175 also receives the bubble signal on line 143 from which CPU 175 may detect air in the syringe neck and take appropriate action, and in addition, CPU 175 receives the bubble detection oscillator signal on line 151, which can be used as noted above to confirm proper operation of the oscillator in the air detection module 122. Further, CPU 175 receives the output of flag sensor 63, from which CPU 175 may determine whether the face plate is securely locked to the housing of power head 14. Furthermore, CPU 175 receives digital signals from the three magnetic detectors 57a, 57b and 57c indicative of which of several possible face plates are mounted to power head 14, allowing CPU 175 to adjust its operation accordingly.

CPU 175 also receives digital input signals from parallel rotary encoders 182, which produce pulse signals on lines 183a and 183b indicative of rotation of the plunger drive train. These pulses are used by CPU 175 to confirm movement of the plunger drive ram. Lines 183a and 183b are also connected to the power pack (see FIG. 4C) so that the power pack CPU may perform closed loop control of plunger movement by counting encoder pulses and comparing the rate of receipt of encoder pulses to a desired rate. A closed loop control is disclosed in U.S. Pat. No. 4,812,724, which is incorporated by reference herein in its entirety.

CPU 175 also produces multiple digital control signals, including those noted above, i.e., the air bubble detector power PWM signal on line 145, and the heater blanket power PWM signal on line 166, both being pulse-width modulated by CPU 175 to produce desired power levels. CPU 175 further produces output signals on lines 187 for illuminating light emitting diodes in lamp 45 (FIG. 2) which indicate the status of operation of the injector. Additional output signals on SPI serial bus lines 156 control the display 30.

CPU 175 uses the above-noted inputs and outputs to perform primary control of power head 14 under control of software resident in CPU 175 or read from RAM 178. As noted above, CPU 175 is also connected, through SPI serial bus 156, to a microcontroller 192 which serves as a monitor, for monitoring operation of CPU 175 to ensure the absence of software or hardware failures. (Microcontroller may be a single-chip microcontroller available from Microchip Technologies as part no. PIC16C63.) Monitor microcontroller 192 performs this function by receiving, through bus 156, an indication of the current operational state of CPU 175.

Specifically, CPU 175 indicates, through bus 156, the operating state of CPU 175, i.e., whether CPU 175 is requesting movement of the plunger or not, and whether the motion is being requested in response to hand-operated or automatic (programmed) control, and potentially other specific information such as the rate of movement that is being requested. Monitor microcontroller 192 reads this state information from lines 156, and compares this information to crucial digital input signals from the power head 14, to ensure consistency therebetween.

For example, microcontroller 192 receives the safe signal on line 115 and home signal on line 117. If these signals indicate that the hand-operated controls are not being used, then CPU 175 should not be generating movement under hand-operated control. If a spring has failed (as indicated by the signal on line 115), this should be reflected in the state of the CPU 175. Therefore, under these conditions, microcontroller 192 reads the state information from bus 156 to ensure that CPU 175 is not acting inconsistently with the signals from the hand-operated controls.

As a second example, microcontroller 192 receives the output signals from rotary encoders 182 on lines 183a and 183b. Microcontroller 192 checks these signals to determine whether the plunger drive ram is moving, to ensure the drive ram is moving only when the state of CPU 175 indicates that the drive ram should be moving, and not otherwise. Furthermore, in this connection it should be noted that microcontroller 192 receives the door flag signal from door flag sensor 63. If this signal indicates that the door of power head 14 is other than in the locked position, CPU 175 should not be requesting movement of the plunger drive ram, and microcontroller 192 confirms this by checking for the absence of pulses from encoders 182.

Figure 4C:
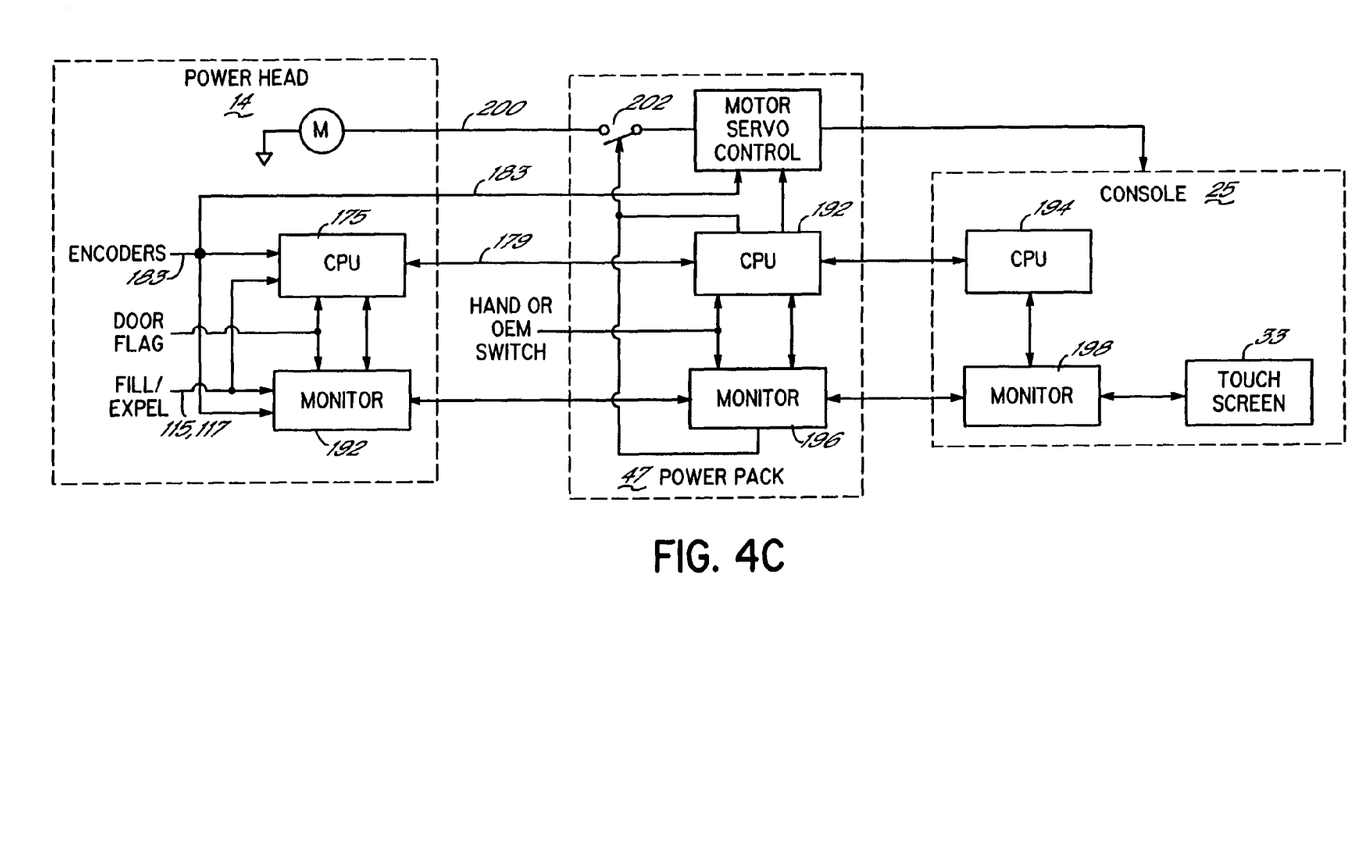
FIG. 4C is an electrical block diagram of the watchdog system of the injector of FIG. 1.

Referring now to FIG. 4C, the interaction of the power head 14, power pack 47 and console 25 can be further understood. Specifically, each of power head 14, power pack 47 and console 25 contains a CPU 175, 192 and 194, respectively. These CPUs interact through external interfaces to perform control of the injector. For example, the plunger drive ram can be controlled through the lever 16 on power head 14 (as discussed above), or can be automatically controlled by an operator entering programs for injections using touch screen 33 of console 25 (using CPU 194), and then enabling the programmed injection. The injection parameters such as motor speed and injection volumes will then be produced by console CPU 194, which communicates with power pack CPU 192 to cause these programmed actions to take place. Furthermore, an automatic injection may be enabled using the touch screen 33, or an injection may be started using a hand switch or OEM remote trigger connected to power pack 47. In either case, the appropriate one of CPUs 192 and 194 generates an enabling signal to initiate the automatic injection.

As noted above, the power head CPU 175 is associated with a monitor microcontroller 192 for monitoring the state of CPU 175 to ensure its actions are consistent with input signals from power head 14. Similarly, CPUs 192 and 194 are also associated with monitor microcontrollers 196 and 198, respectively, which monitor the actions of the associated CPUs 196 and 198 to ensure consistent, error free behavior.

Monitor microcontrollers 192, 196 and 198 communicate with each other in a manner which parallels the communication of CPUs 175, 192 and 194. Specifically, the three monitor microcontrollers exchange state information received from their associated CPUs to ensure that the three CPUs are in similar states of operation; e.g., hand-operated movement, automatic movement, no movement, etc. Furthermore, each of the microcontrollers receives external input signals to ensure that state transitions which should occur are, in fact, occurring. Thus, microcontroller 196 receives the hand or OEM trigger signals so that microcontroller 196 can determine when an automatic injection has been triggered. Microcontroller 198 receives input signals from touch screen 33 so it, too, can determine when an automatic injection has been triggered. Other monitoring functions can be performed, as desired to ensure correct and consistent operation of CPUs 175, 192 and 194.

As noted above, power head CPU 175 delivers a control signal to power pack 47, requesting a ram movement. Power pack 47 contains the motor servo control circuitry for producing an appropriate power signal on line 200 to the drive motor M, and to perform closed loop control of motor movements in response to encoder pulses on lines 183.

In error conditions, the monitor microcontrollers can discontinue power flow to the motor M through a hardware disable, represented by switch 202 in series with power line 200, thereby ceasing any movement of the plunger drive. This hardware disable ensures that the monitor microcontrollers can prevent erroneous injection of fluid under error conditions.

Returning now to FIGS. 1-3, operation of the hydraulic remote 12 can be reviewed. The hydraulic remote 12 may be used to control the injection of fluids by the medical injector 10 when a plunger 62 on the remote 12 is moved into a syringe body 64 of the remote 12. The syringe 50 and conduit 52 are filled with air whereby motion of the plunger 62 creates a pressure which is sensed by the pressure transducer 54. When the plunger 62 is moved further into the syringe body 64, the pressure transducer 54 senses a positive change in pressure from the remote 12. In response to the sensed pressure, the control circuit 42 of the injector 10 causes the drive motor to move the plunger drive ram into the syringe 24 on the power head 14 to expel fluid from the syringe 24. In an exemplary embodiment, the control circuit 42 causes the plunger drive ram to expel fluid from the syringe 24 at a rate that is related to the amount of pressure change sensed by the pressure transducer 54. In another exemplary embodiment, the plunger drive ram is moved at a rate proportional to the amount of pressure change.

In the illustrated embodiment, two pressure transducers 54a, 54b are coupled to the control circuit 42 of the injector to sense pressure from the hydraulic remote 12. The control circuit 42 responds to the pressure sensed by a first of the pressure transducers 54b to control the motion of the plunger drive ram into the syringe 24, as described above. The pressure sensed by the second of the transducers 54a is compared by the control circuit 42 to a threshold pressure above which the injector 10 is enabled and below which the injector 10 is inoperable. This configuration allows the injections to be stopped when an operator releases the plunger 62 on the hydraulic remote 12.

The hydraulic remote 12 may include a feature permitting the plunger 62 to be retracted from within the syringe body 64 of the remote 12. For example, the plunger 62 may include a thumb ring which permits an operator to pull as well as push on the plunger 62. Because the syringe 50 and conduit 52 described herein may be available as off-the-shelf items and therefore readily available, these components of the remote 12 are relatively inexpensive and therefore introduce minimal cost when used as disposable items.

Medical injectors which are presently in use may be modified to use the hydraulic remote 12 of the present invention by incorporation of a circuit board 56 having at least one pressure transducer 54, as described above. The circuit board 56 may generally be added to an existing unit's control circuit 42 to permit the injector 10 to operate with the hydraulic remote 12 and with minimal or no impact to existing software. FIG. 2 shows an exemplary electronic circuit board, including at least one pressure transducer 54, which may be added to existing control circuits 42 of medical injectors 10 to enable the injector 10 to operate with the hydraulic remote 12, as described above.

A method of controlling a medical fluid injector 10 using a hydraulic remote 12 as described above, includes the steps of moving a plunger 62 of the hydraulic remote 12 to generate a pressure, sensing the pressure generated by the hydraulic remote 12 and moving a plunger drive ram on the injector 10 in response to the sensed pressure, whereby the medical fluid injector 10 ejects fluid from a syringe 24 coupled to the injector 10 unit. In an exemplary embodiment, the control circuit 42 causes the plunger drive ram to eject fluid from the syringe 26 on the injector 10 unit at a maximum rate of about 6 ml/sec in response to a pressure sensed by the pressure transducer 54.

While the present invention has been illustrated by the description of the various embodiments thereof, and while the embodiments have been described in considerable detail, it is not intended to restrict or in any way limit the scope of the appended claims to such detail. For example, while the medial injector 10 has been described herein as being configured to inject fluids into a patient in response to movement of the plunger 62 on the hydraulic remote 12 into the syringe body 64, it is also contemplated that the medical injector 10 could also be configured to aspirate fluids from a patient in response to movement of the plunger 62 out of syringe body 64. The injector 10 could be configured to perform either of these functions, solely or selectively, according to the desired operation. For example, it may be desired to aspirate a small amount of blood from a patent upon initial catheterization to confirm that the intravascular space has been entered.

Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of Applicant's general inventive concept.

What is claimed is:

1. A medical fluid injector, comprising:
   a syringe including a motor-driven plunger;
   a control circuit, wherein an output of said control circuit controls movement of said motor-driven plunger;
   a first pressure transducer operatively connected to said control circuit;
   a hydraulic syringe actuator operable to actuate said syringe through said control circuit;
   a conduit extending from said hydraulic syringe actuator to said first pressure transducer; and
   a fluid within said conduit;
   said hydraulic syringe actuator being responsive to a control pressure manually exerted by a user on said hydraulic syringe actuator, said first pressure transducer sensing a change in pressure in said conduit produced by application of said control pressure on said hydraulic syringe actuator, and said control circuit being responsive to said sensed pressure change to control movement of said motor-driven plunger.

2. The medical fluid injector of claim 1, wherein said control pressure is generated in a fluid medium that is directly controlled by the user.

3. The medical fluid injector of claim 1, wherein said hydraulic syringe actuator actuates said syringe to inject fluid when said control pressure is greater than a reference pressure.

4. The medical fluid injector of claim 1, wherein said hydraulic syringe actuator comprises a second syringe.

5. The medical fluid injector of claim 1,
wherein said first pressure transducer is operable to generate a first signal associated with said control pressure; and
said hydraulic syringe actuator controlling movement of said motor-driven plunger based on said first signal.

6. The medical fluid injector of claim 1, wherein said first pressure transducer generates a first signal associated with said control pressure, the medical fluid injector further comprising:
a second pressure transducer operable to generate a second signal associated with a reference pressure;
said hydraulic syringe actuator controlling movement of said motor-driven plunger based on said first and second signals.

7. The medical fluid injector of claim 1, wherein the medical fluid injector was not originally configured to operate with said hydraulic syringe actuator, the medical fluid injector further comprising:
a circuit board coupled to the medical fluid injector to modify the originally configured injector such that it can be used with said hydraulic syringe actuator.

8. The medical fluid injector of claim 1, wherein said syringe effects a powered injection or withdrawal of fluid at a rate related to said control pressure.

9. The medical fluid injector of claim 1, wherein said syringe effects a powered injection or withdrawal of fluid at a rate that is proportional to said control pressure.

10. The medical fluid injector of claim 1, wherein said first pressure transducer provides a sensed control pressure signal to said control circuit, and wherein said control circuit is responsive to said sensed control pressure signal to control said motor-driven plunger based upon said sensed control pressure signal.

11. The medical fluid injector of claim 1, wherein said first pressure transducer generates a first signal associated with said control pressure, the medical fluid injector further comprising:
a second pressure transducer operatively connected to said control circuit, wherein said conduit extends from said hydraulic syringe actuator to said second pressure transducer, and wherein when said control pressure sensed by said second pressure transducer satisfies a preset threshold, operation of the medical fluid injector by said hydraulic syringe actuator is enabled and is based upon said first signal.

12. The medical fluid injector of claim 1, wherein said control circuit is configured to allow both manual control of said motor-driven plunger by said hydraulic syringe actuator and programmed control of said motor-driven plunger.

13. The medical fluid injector of claim 1, wherein said hydraulic syringe actuator comprises a second syringe, and wherein said second syringe and said conduit each comprise air.

14. The medical fluid injector of claim 1, further comprising:
a circuit board comprising said first pressure transducer, wherein said circuit board is separate from and operatively connected with said control circuit.

15. A medical fluid injector comprising:
a drive motor having a plunger drive ram;
a syringe having a syringe barrel and a plunger disposed within and movable relative to the syringe barrel, wherein the plunger drive ram of the drive motor is designed to couple with the plunger of the syringe such that the drive motor is adapted to move the plunger within and relative to the syringe barrel to inject contents of the syringe or to draw fluid into the syringe;
a first pressure transducer;
a hydraulic remote operable to actuate the drive motor;
a conduit extending from the hydraulic remote to the first pressure transducer; and
a fluid within the conduit, wherein operation of the drive motor is responsive to a control pressure manually exerted by a user on the hydraulic remote and sensed by the first pressure transducer through sensing a resulting change in pressure in said conduit, and wherein the drive motor effects a powered injection of fluid with the syringe at a rate related to the control pressure exerted by the user on the hydraulic remote and sensed by the first pressure sensor.

16. The medical fluid injector of claim 15, wherein the control pressure is generated in a fluid medium that is directly controlled by the user.

17. The medical fluid injector of claim 15, wherein the hydraulic remote actuates the drive motor to inject fluid when the control pressure is greater than a reference pressure.

18. The medical fluid injector of claim 15, wherein the first pressure transducer is operable to generate a first signal associated with the control pressure, and wherein the hydraulic remote controls movement of the plunger by the drive motor based on the first signal.

19. The medical fluid injector of claim 15, wherein the first pressure transducer is coupled to a circuit board and operable to generate a first signal associated with the control pressure, and wherein the medical fluid injector further comprises:
a second pressure transducer coupled to the circuit board and operable to generate a second signal associated with a reference pressure, wherein the hydraulic remote controls movement of the plunger by the drive motor based on the first and second signals.

20. The medical fluid injector of claim 15, wherein the medical fluid injector was not originally configured to operate with the hydraulic remote, and wherein the medical fluid injector further comprises:
a circuit board to modify the originally configured injector such that it can be used with the hydraulic remote.

21. The medical fluid injector of claim 15, wherein the hydraulic remote is designed to provide tactile feedback to a user that is indicative of a rate and volume of injection or fluid withdrawal.

* * * * *